(12) United States Patent
Schöggler (10) Patent No.: US 11,801,160 B2
(45) Date of Patent: Oct. 31, 2023

(54) DEVICE FOR COOLING A BODY REGION

(71) Applicant: AUROX GMBH, Graz (AT)

(72) Inventor: Christoph Schöggler, Graz (AT)

(73) Assignee: AUROX GMBH, Graz (AT)

( * ) Notice: Subject to any disclaimer, the term of this patent is extended or adjusted under 35 U.S.C. 154(b) by 984 days.

(21) Appl. No.: 16/342,403

(22) PCT Filed: Oct. 17, 2017

(86) PCT No.: PCT/AT2017/060265
§ 371 (c)(1),
(2) Date: May 23, 2019

(87) PCT Pub. No.: WO2018/071933
PCT Pub. Date: Apr. 26, 2018

(65) Prior Publication Data
US 2019/0274873 A1    Sep. 12, 2019

(30) Foreign Application Priority Data

Oct. 17, 2016  (AT) .................................. 50939/2016

(51) Int. Cl.
*A61F 7/00* (2006.01)
*A61F 7/02* (2006.01)

(52) U.S. Cl.
CPC ............... *A61F 7/007* (2013.01); *A61F 7/02* (2013.01); *A61F 2007/0002* (2013.01);
(Continued)

(58) Field of Classification Search
CPC .... A61F 7/007; A61F 7/02; A61F 2007/0002; A61F 2007/0006; A61F 2007/0007;
(Continued)

(56) References Cited

U.S. PATENT DOCUMENTS 4,470,263 A * 9/1984 Lehovec .................. A42C 5/04
62/3.5
4,585,002 A * 4/1986 Kissin ..................... A61F 7/007
607/96
(Continued)

FOREIGN PATENT DOCUMENTS

AT       511263      8/2014
CN      2337480      9/1999
(Continued)

OTHER PUBLICATIONS

Japan Office Action conducted in counterpart Japan Appln. No. 2019-541826 (dated Aug. 31, 2021) w/ translation.
(Continued)

*Primary Examiner* — Tigist S Demie
(74) *Attorney, Agent, or Firm* — GREENBLUM & BERNSTEIN, P.L.C.

(57) ABSTRACT

The invention relates to an device (1) for cooling and/or heating a body region, preferably a head region, comprising at least one thermally conductive skin contact material (2) and at least one Peltier element (3), wherein the Peltier element (3) is connected to the skin contact material (2), wherein a thermally conductive connecting element, in particular a thermally conductive film (5), and a heat dissipation element (12) are provided, wherein heat emitted via an outer side of the Peltier element (3) can be distributed to the heat dissipation element (12) via the connecting element.

13 Claims, 6 Drawing Sheets

(52) U.S. Cl.
CPC ............... *A61F 2007/0006* (2013.01); *A61F 2007/0007* (2013.01); *A61F 2007/0075* (2013.01); *A61F 2007/0225* (2013.01); *A61F 2007/0226* (2013.01); *A61F 2007/0228* (2013.01)

(58) Field of Classification Search
CPC ...... A61F 2007/0075; A61F 2007/0225; A61F 2007/0226; A61F 2007/0228
See application file for complete search history.

(56) References Cited

U.S. PATENT DOCUMENTS

| | | | |
|---|---|---|---|
| 5,970,718 A * | 10/1999 | Arnold | A61F 7/10 62/3.5 |
| 2008/0300529 A1 * | 12/2008 | Reinstein | A61F 7/007 604/20 |
| 2013/0116759 A1 | 5/2013 | Levinson et al. | |
| 2015/0209174 A1 * | 7/2015 | Abreu | A61F 7/02 607/104 |
| 2015/0335466 A1 * | 11/2015 | Schöggler | A61F 11/08 607/109 |
| 2016/0178251 A1 | 6/2016 | Johnson et al. | |
| 2016/0213905 A1 | 7/2016 | Abreu | |
| 2017/0095367 A1 * | 4/2017 | Lini | A61F 7/007 |

FOREIGN PATENT DOCUMENTS

| | | |
|---|---|---|
| CN | 2532706 Y | 1/2003 |
| CN | 103068346 | 4/2013 |
| CN | 203138805 | 8/2013 |
| CN | 103948467 | 7/2014 |
| CN | 204072453 U | 1/2015 |
| CN | 104334128 | 2/2015 |
| CN | 104780949 A | 7/2015 |
| CN | 105246419 | 1/2016 |
| EP | 0 050 473 | 4/1982 |
| JP | 57-104069 A | 6/1982 |
| JP | 1-270866 A | 10/1989 |
| JP | 2016-120268 | 7/2016 |
| WO | 2014/059454 | 4/2014 |
| WO | 2015/106180 | 7/2015 |
| WO | 2015/145471 | 10/2015 |
| WO | WO-2015145471 A1 * | 10/2015 ............. A61F 7/007 |
| WO | 2016/160691 A1 | 10/2016 |

OTHER PUBLICATIONS

China Office Action conducted in counterpart China Appln. No. 201780077814.7 (dated Dec. 30, 2020) w/ translation.
Second China Office Action conducted in counterpart China Appln. No. 201780077814.7 (dated Sep. 1, 2021) w/ translation.
Int'l Search Report (Form PCT/ISA/210) conducted in Int'l Application No. PCT/AT2017/060265 (dated Jan. 17, 2018).
Int'l Written Opinion (Form PCT/ISA/237) conducted in Int'l Application No. PCT/AT2017/060265 (dated Jan. 17, 2018).
Austria Office Action conducted in counterpart Austria Appln. No. A50939/2016 (dated Jun. 1, 2017) (w/ machine translation).
Japanese Patent No. JP 7074401 = B2 (counterpart of the instant application), dated May 24, 2022, along with English translation.
Office action of family member Chinese Patent Application No. 201780077814.7, the Office action dated Dec. 13, 2022.
Note: the following three documents cited in the Chinese Office action were previously made of record in the instant application: (1) US 2008/0300529-A1; see the Information Disclosure Statement filed on May 13, 2019, and the final Office action dated Nov. 1, 2022; (2) WO 2015/145471-A1; see the Information Disclosure Statement filed on May 13, 2019, and see the non-final Office action dated Mar. 15, 2022; and (3) EP 0 050 473-A2; see the Information Disclosure Statement filed on May 13, 2019.
Office action in the corresponding European patent application No. 17 791 277.1-113, dated Jul. 24, 2023, along with an English language translation.

* cited by examiner

DEVICE FOR COOLING A BODY REGION

BACKGROUND

1. Field of the Invention

The invention relates to a device for cooling and/or heating a body region, preferably a head region, comprising at least one thermally conductive skin contact material and at least one Peltier element, wherein the Peltier element is connected to the skin contact material.

2. Description of the Background

Each year, many thousands of cosmetic surgeries are performed, for example, on the nose. After a nose operation, a 3-mm to 5-mm thin plaster cast is placed over the nose for post-operative care. In addition to a medicinal therapy, doctors also recommend a cooling and drainage of the nose in order to achieve a rapid alleviation of pain and a quick healing of the wound and scar. An ice pack is often used for the cooling and relief of swelling.

A disadvantage when using an ice pack is that the ice pack soaks through a plaster cast or bandage, which is why the cast or bandage must be frequently changed. Furthermore, a cooling temperature cannot be regulated with an ice pack, and is also too low in most cases. It has been shown that, for a cooling of a swollen body region such as a nose in order to promote healing, the temperature must not be allowed to fall below a certain level. Temperature decreases that are too large and persist for longer periods during a use of an ice pack are not desired, since a patient can experience negative effects such as pain, numbness and other sensory disorders.

SUMMARY

This is addressed by the invention. The object of the invention is to specify a device of the type named at the outset with which a body region can be individually and efficiently cooled with little effort.

According to the invention, the object is attained in that, with a device of the type named at the outset, a thermally conductive connecting element, in particular a thermally conductive film, and a heat dissipation element are provided, wherein heat emitted via an outer side of the Peltier element can be distributed to the heat dissipation element via the connecting element.

One advantage achieved with the invention in particular is that heat on an outer side of the Peltier element can be transferred, indirectly or directly, preferably by direct contact, to the connecting element and that the heat can, via said element, subsequently be distributed or transferred to the heat dissipation element and can then be dissipated outward via the heat dissipation element. Alternatively, the skin contact material can be heated by means of the Peltier element. A specific body region that is in contact with the skin contact material can thus be heated. This also enables different temperature profiles on each individual skin contact material. For this purpose, the skin contact material can be embodied as skin contact plates, for example. A device according to the invention can, for example, comprise one or more skin contact plates of this type.

The thermally conductive connecting element is preferably embodied to be flexible and is formed from a heat spreader material, for example, from graphite or copper. The connecting element can, for example, be embodied as a thermally conductive film such as a graphite film or copper sheet. However, in most cases, the connecting element is embodied as a flexible thermally conductive pad. A thermally conductive film embodied as a graphite film is embodied to be bendable or flexible and ultra-thin. The thermally conductive connecting element is suitable for dissipating heat on an outer side of the Peltier element, wherein the connecting element is arranged between the at least one Peltier element and the heat dissipation element embodied, for example, as an aluminum sheet. With a conductive thermally conductive film or thermally conductive pad or thermally conductive paste, heat can be further distributed across a large area, in particular to the heat dissipation element provided for dissipating the heat. It is particularly preferred if the connecting element is directly connected to an outer side of a circuit board. The thermally conductive connecting element is in particular embodied to be planar, so that said element comprises a large portion of an area of the device. A cross-sectional area of the thermally conductive film is at least the same size as, but preferably several times larger than, a cross-sectional area of the at least one Peltier element. It can be provided that the planar and thin thermally conductive film extends from a first Peltier element to a next or second Peltier element. Alternatively, the thermally conductive connecting element can also be embodied as a heat-conducting paste or thermally conductive paste that connects the Peltier element to the heat dissipation element. A cross-sectional area of such a paste thereby essentially corresponds to the area of the Peltier element. If multiple Peltier elements are provided, a thermally conductive paste is provided between each Peltier element and the heat dissipation element. The heat dissipation element is preferably embodied to be planar and extends in particular across a large portion of the device. It is particularly preferred that the heat dissipation element is embodied to be flexible and/or bendable. For this purpose, it can be provided, for example, that the heat dissipation element is made of an aluminum sheet. If necessary, two or more heat dissipation elements can also be provided. For the heat dissipation element to be embodied to be flexible, it can be provided that said element is made of a flexible material. Alternatively, the heat dissipation element can be embodied in multiple parts, wherein the parts are connected in a bendable manner.

With the Peltier element, it is possible to bring the thermally conductive skin contact material to a specific temperature and to thus ensure an ideal healing of a swollen body region. For example, a nose that has been operated on can be cooled in an individually adapted manner, in particular on the nasal bone, lateral cartilage, alar cartilage, cheekbone area, and on the cheekbones. The skin contact material is in particular made of a metal, preferably aluminum, copper, titanium or a corresponding alloy with a metal of this type. It is particularly preferred if the skin contact material is made of a bendable metallic film, for example, a silvered copper film or an anodized or silver-coated aluminum plate. The skin contact element can also be made of a copper plate that is silvered in a first step and rhodium-plated in a second step, or of a gold-plated plate. The skin contact material can also be made of palladium or a different metal. Alternatively, it can also be beneficial if the skin contact element is made of multiple small, rigid metal sheet elements. As a result, the skin contact material can be adapted to a shape of the body region that is to be cooled, whereby the body region can then be evenly cooled.

Via the Peltier element, heat can be extracted from the body region that is to be cooled. If multiple body regions, such as both cheekbone areas for example, are to be cooled, one skin contact material and one Peltier element are provided for each body region that is to be cooled. If multiple Peltier elements are provided, it is possible that these elements can be activated independently from one another, wherein the Peltier elements can be embodied to be dependent on or independent from one another.

The wearable device advantageously comprises a thermally conductive layer structure with which heat can be emitted outward, wherein the layer structure is embodied to be at least partially flexible. Thus, the wearably embodied device can be flexibly adapted to a body region that is to be cooled and heat can be dissipated outward via the layer structure.

It is advantageous if the device is embodied to be free of liquid heat transfer media. In this manner, a moistening of the region that is to be cooled and, for example, of a cast or other bandage material, as well as of the skin and hair of a patient, is avoided. In addition, it is beneficial if the device is free of turbomachines such as fans, ventilators and the like.

It is advantageous if a circuit board is provided. The circuit board is in particular embodied to be at least partially flexible. Alternatively, the circuit board comprises for example two, three, four or more rigid parts that are connected to one another with flexible cables or the like. It is further advantageous if the circuit board comprises multiple electronic components and extends in particular across an entire area of the device, whereas the Peltier element is embodied to be smaller. Heat that is to be dissipated can thus be distributed across a large area, and an efficient cooling can therefore be rapidly carried out. No liquid heat transfer media and no fan and/or ventilator are provided or necessary. The device is embodied for cooling a body region, for example a head region or nose region, in particular after an operation. It is in particular advantageous if the circuit board is embodied with one or more thermal vias in order to enable a heat dissipation through an, in particular thermally insulating, circuit board material such as FR-4, for example. Additionally, a cover made of a thermally conductive material, for example a thin aluminum sheet, in particular with a thickness of approximately 0.2 mm, can be arranged on the circuit board, which material dissipates heat from the vias to an ambient air. Furthermore, a smooth, safe and in particular skin-compatible surface can be provided with this cover.

Expediently, the circuit board thereby extends from one Peltier element to the next. However, the circuit board can also be interrupted by wire connections or two parts of the circuit board can be connected by a wire connection. Furthermore, it can be provided that the circuit board is arranged in a continuous manner across a hot side of the Peltier element. Due to the at least partially flexible embodiment of the circuit board, the circuit board can be adapted to a shape of the body region that is to be cooled, so that the body region that is to be cooled can be cooled individually and efficiently. The at least one Peltier element can be activated and controlled via the circuit board, which enables an individual cooling. A flexible insulating material can also be provided which essentially extends across an entire area of the device and in which the Peltier element is embedded. The insulating material is embodied to protect the Peltier element and other elements of the device against damage and wear. The circuit board is advantageously arranged on the outer side of the insulating material. The skin contact material preferably has a larger area than the Peltier element and extends across a bottom side of the insulating material in order to consequently cool a body region. The insulating material can, for example, be made of latex, silicone, or another soft plastic, or from a combination of different plastics. Alternatively, the insulating material can also be made of or comprise a rigid plastic. In particular, the insulating material is made of a thermoplastic elastomer such as a thermoplastic polyurethane. For improved thermal insulation, a plastic film can also be inserted in order to avoid a thermal feedback. Furthermore, the skin contact material is always arranged on the device such that the skin contact material is directly in contact with the body region that is to be cooled. Since temperature profiles can be precisely controlled using the Peltier element, the device can also be used for a slight heating, for example, in a hot and cold therapy. The device is in particular embodied such that cooling profiles are possible. For this purpose, all cooling surfaces can be freely regulated and controlled so that any desired cooling curve can be applied to a desired site.

It is further advantageous if at least one cooling body is provided in order to emit to the air the heat dissipated by the skin by means of thermal conduction or free convection. The cooling body can be embodied to be rigid and/or stiff or slightly flexible. The cooling body is advantageously made of a metal, in particular an aluminum or copper sheet, which exhibits good thermal conductivity and is not embodied to be fully rigid.

It is expedient if an energy source is provided for operating the Peltier element, wherein the energy source is in particular connected to the Peltier element via cables. Alternatively or additionally, the energy source can also be connected to the Peltier element via the circuit board. The energy source can be embodied as a storage battery and indirectly connected via cables to the Peltier element to supply power to said element. In particular, an external energy source is provided. However, it can also be provided that an energy source, such as one or more batteries or storage batteries, is embedded in the device. Cables of the Peltier element are preferably clipped off near said element and are electrically connected to the circuit board. It can in particular be provided if the energy source is encased in a plastic housing or storage battery housing, for example, made of a thermoplastic elastomer that is preferably skin compatible.

It is furthermore beneficial if a control unit is provided. The control unit is connected to the Peltier element and to the energy source so that the Peltier element can be controlled and regulated. As an alternative to the control unit, or in addition thereto, a regulating unit can be provided. The control unit and/or regulating unit can, in principle, be arranged in any desired position; however, it is expedient if the unit is arranged between the energy source and the device. The control unit monitors and regulates temperatures at which a body region is to be cooled. Cooling sequences can thus be designed in any desired manner; for example, it is possible to set an interval cooling or a cooling at a constant temperature. In addition, the control unit allows a specification of specific maximum values and/or minimum values for the temperature, so that a desired temperature range can be set for an individual therapy. An undesired undershooting of a minimal temperature can thus be avoided, for example. Furthermore, a patient can individually match any desired therapy temperature to his/her condition. It is particularly preferred if temperature values and/or temperature profiles are variably programmable or settable. In addition, external signals from the body, environment and/or ambient surroundings can be incorporated into a program sequence. The device or control unit can also be embodied to be adaptive. Bodily functions, such as an oxygen content in the blood and/or a skin resistance, for example, as well as external signals such as a light intensity, a sound level and/or vibrations can thus be monitored. Furthermore, an influence of the weather can thus also be monitored. A probability of headaches or general bodily wellness, for example, varies based on changes in temperature and/or atmospheric pressure. An activation of the control unit for regulating special cooling profiles expediently occurs via a mobile phone or the like, which is connected to the control unit, for example, via Bluetooth Low Energy. The control unit and/or regulating unit expediently comprises a storage battery, an operating element for setting the temperature, and a rectifier for generating direct current. If multiple Peltier elements are provided, it is expedient if they can be activated individually or separately in order to enable different cooling curves in different body regions. In particular, the at least one Peltier element is activated with slow pulses of approximately 1 Hz, in particular approximately 0.7 Hz, particularly preferably approximately 0.5 Hz or less. However, the Peltier element can also be activated with a faster pulse frequency. Furthermore, it can be provided that the device or the control unit can be controlled with an app via a mobile phone, tablet computer or the like. An app of this type offers different curves or data for different ailments, from which a patient or user can select.

If a temperature is to be precisely regulated, it is furthermore beneficial if at least one temperature sensor is provided. In particular, it is beneficial if multiple, for example six, temperature sensors are arranged in different locations on the device. The temperature sensors are thereby preferably arranged close to the skin and the cooling materials. In particular, the at least partially flexible circuit board comprises one or more temperature sensors. Furthermore, at least one temperature sensor can be embodied to measure an ambient temperature. The circuit board can furthermore comprise additional electronic components, for example, sensors for determining a light intensity or bodily functions. In addition, it can be beneficial if actuator devices are provided, for example, a vibration device for massaging the temples.

For therapies that also require a delivery of pharmaceuticals and/or antiseptic agents, it is expedient if a line 24 is provided for a supply of pharmaceuticals. Such line is depicted schematically in FIG. 3, although such line could also be depicted in FIGS. 2 and 4, as well. The line is preferably arranged on an outer surface of the skin contact material. Thus, in a therapy of a body region, substances that promote healing can also be supplied at the same time in addition to a cooling of the body region. Such substances or pharmaceuticals are preferably located in a designated tank and can be dispensed to the skin surface with a targeted control.

It is advantageous if an acoustic output device 23a and/or a vibration output device 23 are provided. These devices, which are depicted schematically in FIG. 1, can be embodied to output various parameters such as warning signals and/or a cooling progress for a patient or an attending physician. The vibration output device preferably comprises one or more vibration motors for generating a vibration signal or vibration signal sequence. A defined vibration signal sequence or vibration pattern can, for example, be coded for a specific parameter, for functions, or for warning signals. The vibration output device thus serves as a feedback system for an overheat or a weak storage battery, for example. Furthermore, it can be provided that the at least one vibration motor can be activated externally, for example, via a smartphone application. In this manner, a vibration can be set in a targeted manner during a cooling phase, for example, so that the vibration has a stimulating or relaxing effect. Alternatively, the Peltier element and/or the at least one vibration motor can be activated by a predefined program that comprises a predetermined temperature profile and/or a predetermined vibration sequence.

It is advantageous if a mount for securing the device to a body region is provided. In principle, it is expedient to cool a body region such as a nose or a forehead in a horizontal body position. However, a cooling of a body region in an upright position can also be provided for. For this purpose, the mount connecting to the device is embodied for securing the device to the head, for example. In this manner, an additional grip or a particularly firm fixing is ensured in order to also enable a use in a seated or standing body position and/or to allow a portable use. The mount is in particular embodied such that an undesired shifting or wiggling of the device is prevented. The device can in principle also be embodied with a shape that allows an independent grip of the device on the body region, so that the device itself serves as a mount.

It is advantageous if the device is constructed in an at least partially layered manner. In particular, the device is embodied as a thermally conductive layer structure that emits heat outward and is also flexible. The skin contact material is thereby connected to the Peltier element on an inner side thereof, wherein the skin contact material is in direct or indirect contact with the body region that is to be cooled. The at least one Peltier element is embedded in an insulating material to which the thermally conductive connecting element or the circuit board connects. The circuit board is arranged on the outer side of the connecting element or vice versa. Closing an outer side, at least one cooling body is provided that is arranged above the Peltier element and can be embodied as an aluminum sheet. An additional rigid cooling element that is conductively connected to the cooling body can also be provided. Additionally, a wire mesh and/or expanded metal can be provided on the same plane. The heat dissipation element is arranged on the outer side of the device, which element is in particular embodied as a plate made of an aluminum alloy, preferably the alloy AlMgSi1. This alloy exhibits similar mechanical properties to spring steel and also has a good or high thermal conductivity. The plate made from an aluminum alloy can furthermore be coated on the outer side with a thin layer of paint. Here, it is expedient if the paint layer is maximally 60 μm thick, in particular maximally 50 μm, preferably 40 μm. The paint layer can comprise a primer and a paint. As an alternative or in addition to the paint layer, the plate can comprise an anodized layer. In addition, it can be provided that the heat dissipation element in particular comprises in a roughly central manner recesses such as slots, circles or the like, so that the heat dissipation element is in this region embodied to be particularly bendable. Alternatively, the heat dissipation element can also be embodied to be thinner in regions, in order to adapt the element to any desired body shape in a targeted manner via predetermined bow points. A material weakening of this type for the predetermined bow points can also occur by means of milled pockets. It is furthermore beneficial if the device is embodied in large part to be bendable so that it can be adapted to the body region that is to be cooled. The individual layers of the device are connected, in particular glued, welded, soldered or joined in another manner, to one another via a thermally conductive adhesive, a thermally conductive film and/or a thermally conductive paste. For example, the connecting element can be embodied as a thermally conductive paste. Alternatively, the individual layers can also be milled from one complete piece.

In principle, the device according to the invention is embodied to be flexible. For this purpose, the predetermined bow points or predetermined bending points can in general be embodied in any desired manner. An articulated connection of individual sections of the device is thereby also possible, though it results in a more complex structure.

BRIEF DESCRIPTION OF THE DRAWING

Additional features, advantages and effects follow from the exemplary embodiments described below. In the drawings which are thereby referenced.

DETAILED DESCRIPTION

Figure 1:
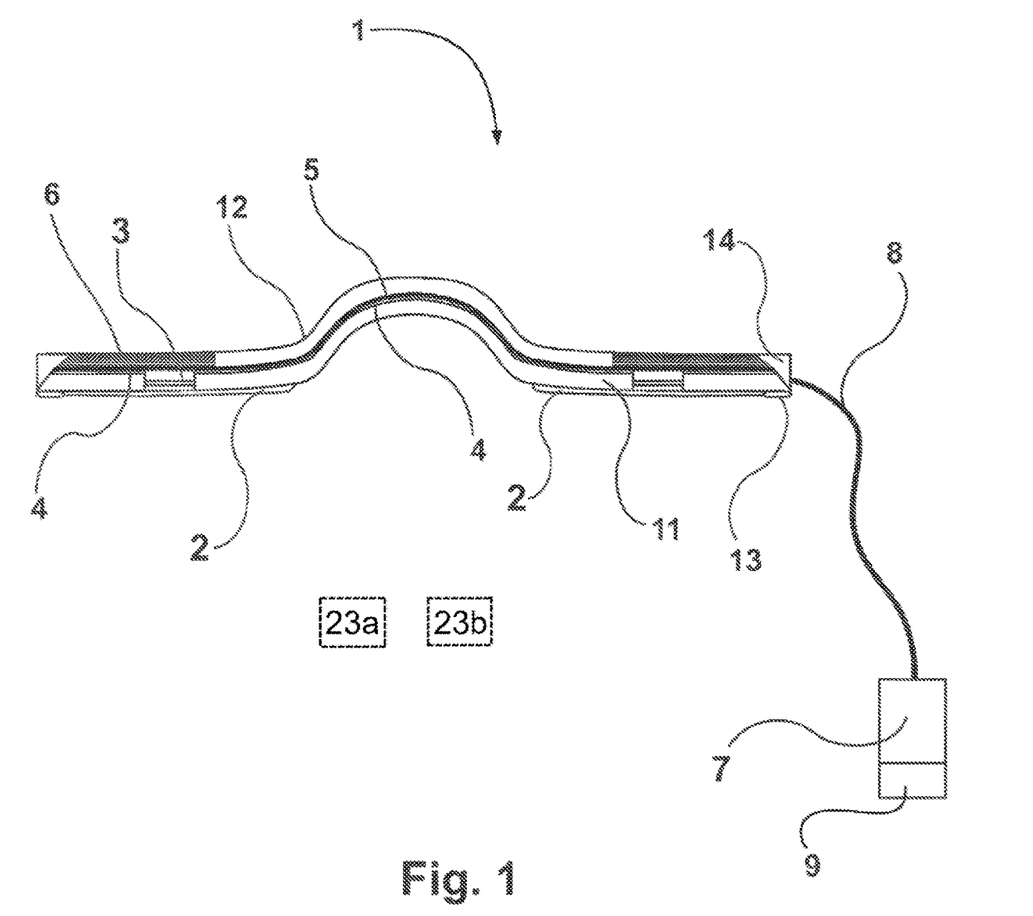
FIG. 1 shows a section through a device according to the invention.

FIG. 1 shows a section through a device 1 according to the invention for cooling a body region, which device is embodied for cooling a nose region. The device 1 is embodied in a layered manner. On a bottom side of the device 1, two skin contact materials 2 are provided which can be arranged on body regions that are to be cooled. Above said materials, one Peltier element 3 each is provided which directly connects to the respective skin contact material 2. The Peltier elements 3 are arranged in a flexible insulating material 11 that can be made of latex, silicone, or another soft plastic, in particular a thermoplastic elastomer such as a thermoplastic polyurethane and comprises a cold and hot side. Connected to the insulating material 11 is a connecting element embodied as a thermally conductive film 5, wherein said element is embodied as a graphite film or essentially as what is referred to as a heat spreader material. In principle, however, the connecting element can also be made of a thermally conductive paste that connects the Peltier element 3 to a heat dissipation element 12. On the outer side of the thermally conductive film 5, an at least partially flexible circuit board 4 is provided. The circuit board 4 advantageously comprises one or more temperature sensors 18 and/or other electronic components not shown in FIG. 1. Both the insulating material 11 and also the thermally conductive film 5 and circuit board 4 are embodied to be at least partially flexible or bendable, so that they can adapt to a shape of the nose region. Furthermore, these elements essentially extend across an entire region of the device 1. In addition, two rigid cooling bodies 6 are provided, wherein between said bodies a heat dissipation element 12 such as a wire mesh is arranged, which element closes the device 1 on the outer side. In place of the wire mesh, an expanded metal or full-area aluminum strip can be provided as a heat dissipation element 12. The heat dissipation element 12 is embodied with varying thickness so that it can be individually adapted to a body region. An inner region of a device 1 of this type can also be embodied to be rigid. To prevent a shifting of the device 1, two anti-slip elements 13 are provided. These elements rest on a skin surface and can be made of latex. In principle, the device 1 can comprise any desired number of anti-slip elements 13. The individual layers of the device 1 are preferably connected to one another in an at least partially materially bonded manner, for example, with thermally conductive adhesive. Additionally, at two lateral ends, a connecting element 14 can be arranged which is made of textile, silicone, or a soft plastic.

In order to supply the Peltier element 3 with energy or power, an energy source 7 preferably embodied as a storage battery 7 is provided which is indirectly connected to the device 1 via a cable 8. Furthermore, a control unit 9 is provided which is preferably locally arranged at the energy source 7 and is connected thereto, and which is also connected to the device via the cable 8. However, the energy source 7 can also be directly integrated in the device 1.

Figure 2:
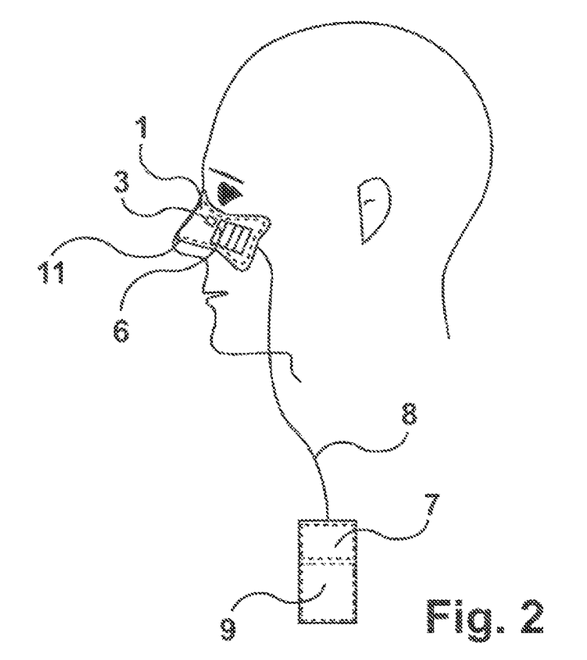
FIG. 2 shows a device according to the invention.

In FIG. 2, the device 1 according to the invention for cooling a body region from FIG. 1 is shown, which device is arranged at the nose region of a patient. The device comprises two skin contact materials 2 and two Peltier elements 3. The skin contact materials 2 are not visible in FIG. 2, since they are respectively arranged between a Peltier element 3 and a skin of the nose region. The illustrated device 1 furthermore comprises two rigidly embodied cooling bodies 6 that are arranged on both sides of the nose. However, it is also possible for only a single cooling body 6 to be provided. In addition, the insulating material 11 is visible in FIG. 2. Furthermore, the external energy source 7 and the external control unit 9 are shown, which are connected to the device 1 via the cable 8. The energy source 7 can, for example, be arrangeable on the neck of a patient, wherein it is permanently connected to the device 1 or can be connected thereto. In additional, cords or the like can be provided for a size-adjustability of the device 1, which cords can be arranged behind the ears of the patient and thus fix the device 1 on the head of the patient. A mount 10, which is not shown, can also be provided in order to secure the device 1 to the head of the patient. A device 1 for cooling a nose region can, for example, be used after a nose operation, a removal of under-eye bags, an eyelid operation, or in the case of facial swelling. Furthermore, the device 1 is suitable for promoting blood circulation and reducing wrinkles or circles around the eyes.

Figure 3:
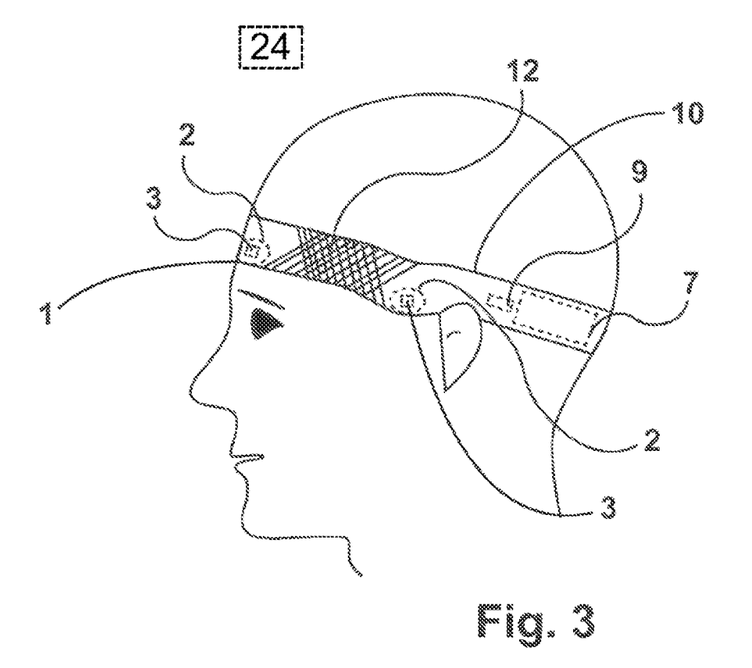
FIG. 3 shows another device according to the invention.
Figure 4:
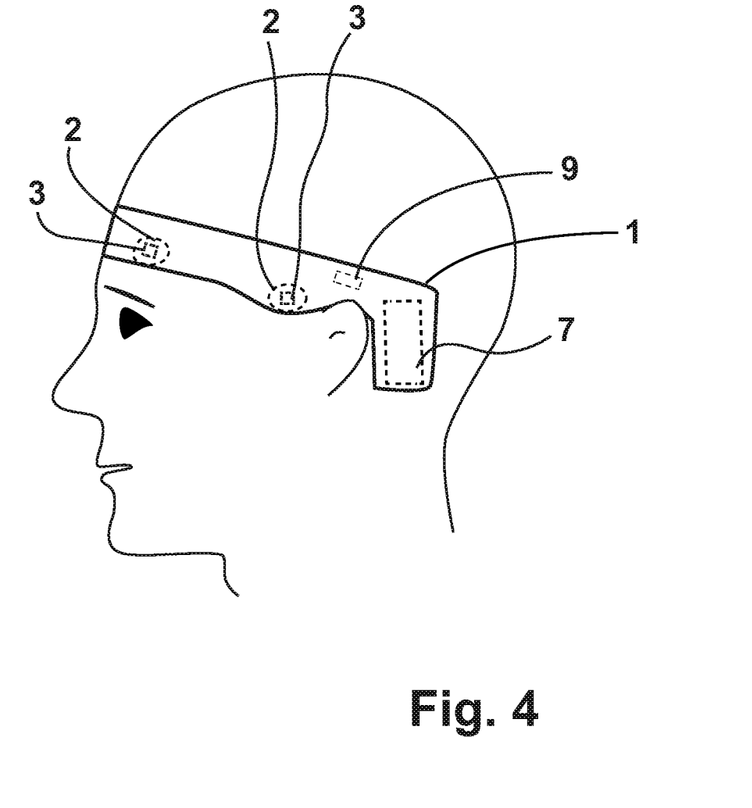
FIG. 4 shows another device according to the invention.

FIGS. 3 and 4 each show another device 1 according to the invention for cooling a body region. These devices are respectively embodied for cooling a forehead and temple region and each comprise multiple skin contact materials 2 and Peltier elements 3. A cooling advantageously takes place on the frontal branch and the roots of the trigeminal nerve, wherein four cooling points are provided. These sites are for this purpose cooled using Peltier elements 3 arranged correspondingly on the device. An energy supply to the Peltier elements 3 occurs via an energy source 7. In addition to the energy source 7, a control unit 9 is provided via which the device 1 can be controlled and regulated. The energy source 7 and the control unit 9 are connected to the Peltier elements 3 via cables 8, wherein cables 8 are routed within the device 1 and are therefore not shown in FIG. 3. The device 1 furthermore comprises a heat dissipation element 12 which can be embodied to be bendable. It is particularly preferable if the heat dissipation element 12 is formed as an aluminum sheet made of the alloy AlMgSi1, which alloy exhibits properties similar to spring steel and also conducts heat well. The device 1 can thus be adapted to different head shapes and head sizes. Furthermore, the device 1 can have a predetermined bow point 21 between the forehead and the temple. In addition, the device 1 shown in FIG. 3 can be secured to the head of a patient via a mount 10. The mount 10 can be made of a textile, silicone, or a soft plastic and fixes the device on the head such that the device does not shift. By contrast, the device 1 shown in FIG. 4 is embodied such that it can be independently fixed on the head of a patient or user without the mount 10 as a result of a clasping effect of the heat dissipation element 12 embodied as an aluminum sheet. This device 1 comprises a sidepiece having an energy source 7, wherein the sidepiece can be arranged behind the ear of a patient in such a way that the device 1 is fixed on the head of the patient. The device 1 thus has a shape similar to spectacles and is embodied to be flexible, so that the device 1 can be put on the patient. Furthermore, in addition to a predetermined bow point 21 between the forehead and temple, the device 1 can also comprise a predetermined bow point 21 in the region of the ear. It can also be provided that a device 1 is integrated into a pair of optical glasses, sunglasses, or virtual reality glasses and/or into a helmet or other wearables.

A device 1 shown in FIGS. 3 and 4 for cooling a forehead and temple region can have a positive effect on various ailments: migraines, headaches, stress, fever, difficulty concentrating, hot flashes, circulatory problems, fatigue, loss of energy, sinusitis, and other ailments. In addition, a device 1 of this type can be used by astronauts in space, since astronauts often suffer from pain in the head region and from nausea and impaired orientation. Another use occurs for fighter pilots, snipers, air traffic controllers and other similar professions. It can also be provided that the individual elements of the device 1 are encased in a sleeve made of plastic, for example, in order to protect the Peltier element 3 and the thermal junctions thereof against mechanical loads. A sleeve made of plastic advantageously has a corresponding flexibility so that the device 1 is embodied to be flexible. In particular, a plastic having a Shore hardness in the range from approximately 50 Shore to 70 Shore is suitable for this purpose, so that an optimum level of adaptability and performance characteristics is ensured.

Figure 5:
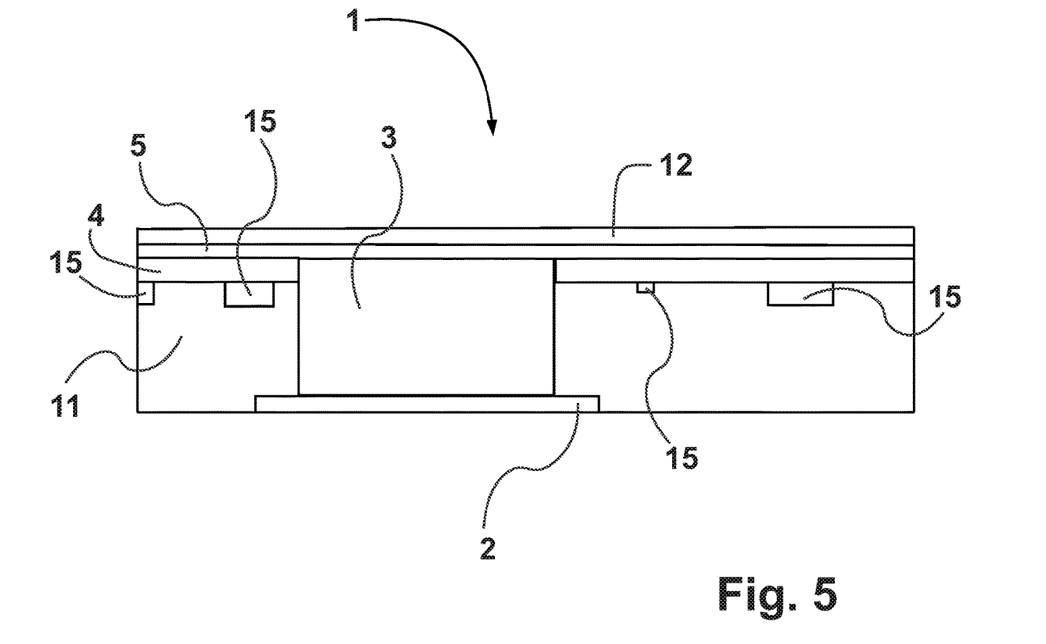
FIG. 5 shows a schematic illustration of a device according to the invention.

In FIG. 5, a schematic illustration of a device 1 according to the invention is shown in which a layer-wise construction of the device 1 is visible. To ensure efficient thermal junctions, individual layers of the device 1 are connected to one another, in particular glued to one another, using a thermally conductive adhesive, a self-adhesive thermally conductive film, a thermally conductive pad 16, and/or a thermally conductive paste. The device 1 constructed in a layered manner comprises, starting from a side resting on a body region that is to be cooled: a skin contact material 2 embodied as an anodized or silvered aluminum plate, a first silvered and then rhodium-plated copper plate, or a nickel-plated and gold-plated copper plate; a Peltier element 3 embedded in an insulating material 11; a circuit board 4 having multiple electronic components 15; a connecting element embodied as a thermally conductive film 5; and a heat dissipation element 12, preferably made of aluminum or an aluminum alloy. The copper plate can, for example, be produced as a deep drawn part.

Figure 6:
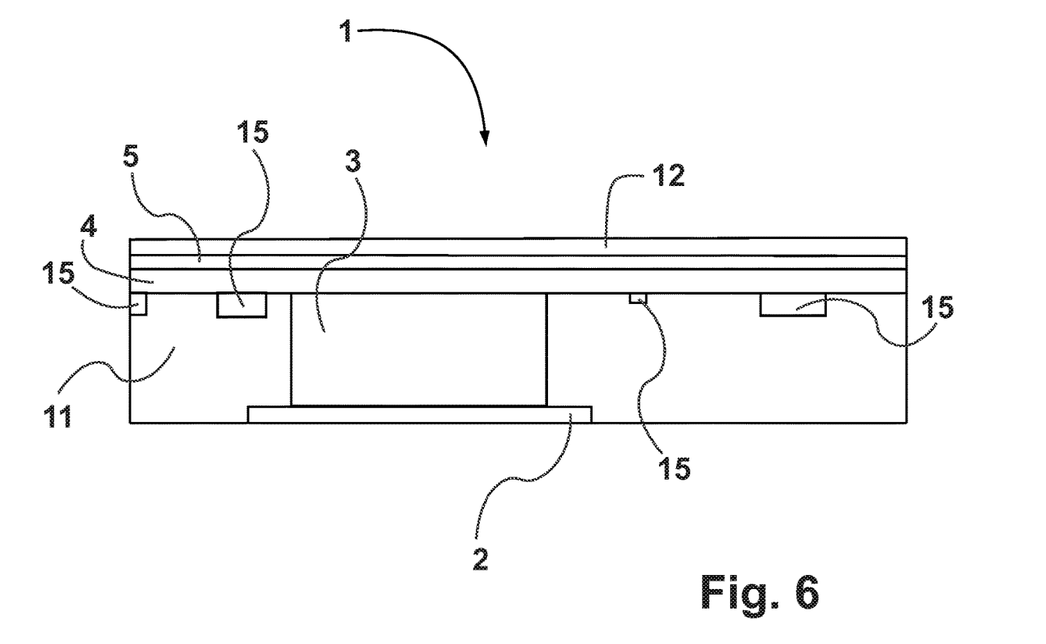
FIG. 6 shows another schematic illustration of a device according to the invention.

FIG. 6 also shows a schematic illustration of a device 1 according to the invention. This device essentially corresponds to the illustration in FIG. 5. In contrast to a device 1 shown in FIG. 5, in this device 1 the circuit board 4 runs all the way through between a hot side of the Peltier element 3 and the thermally conductive film 5 or heat dissipation element 12. Thus, there occurs in this case a heat dissipation to the thermally conductive film 5 and heat dissipation element 12 via the circuit board 4.

Figure 7:
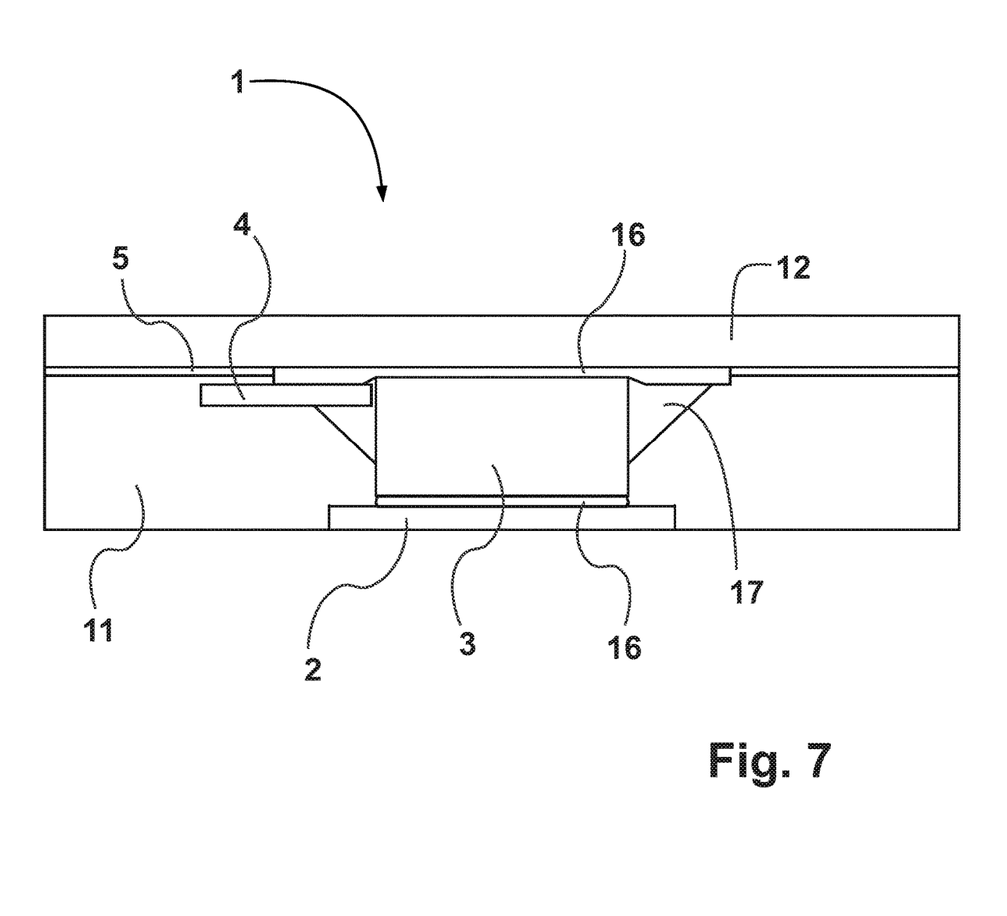
FIG. 7 shows a schematic illustration of another device according to the invention.

A schematic illustration of another device 1 according to the invention is shown in FIG. 7. This device is once again constructed in layers and comprises a skin contact material 2, a Peltier element 3, a circuit board 4 in particular mainly made of copper, an optional thermally conductive film 5, and a heat dissipation element 12. The skin contact material 2 is connected to the Peltier element 3 via a thermally conductive pad 16, which element is also connected to the heat dissipation element 12 via a thermally conductive pad 16. In addition, an insulating material 11 is provided. The device 1 furthermore comprises a hollow space 17 or a space filled with air, in order to thermally decouple a cold and hot side of the Peltier element 3 from one another.

It can furthermore be provided that, in the entire device 1, an electric circuit board 4 is integrated which is constructed from rigid and flexible parts. In this manner, the electronic circuit can be built into the device 1 in a highly integrated manner. A circuit board 4 of this type exhibits a flexibility in the desired locations, whereby significant bending is possible without damage. On the front face of the device 1, the waste heat of the Peltier element 3 is dissipated via a flexible part of the circuit board 4, which part is arranged between two thermally conductive pads. As a result of the flexible part of the electric circuit board 2 being embodied to be very thin at approximately 130 μm, the desired heat dissipation to the surface of the heat dissipation element 12 via the thermally conductive pads is hardly impaired. The circuit board 4 furthermore comprises copper tracks which run through the flexible and rigid part of the circuit board and are electrically connected to one another. As a result, additional electrical components such as temperature sensors 18 can be soldered onto the circuit board 4. Because the copper tracks present on the circuit board 4 also heat up, a temperature sensor 18 soldered thereto will also assume this temperature. Temperatures at the desired locations are thus easily measurable, since the sensors on the flexible part of the circuit board 4 comprise a thermal and electrical connection. Due to the flexibility, parts of the flexible circuit board 4 can be designed such that they can be bent at the desired measuring points and partially tucked into the thermal layer structure. Additionally, an overall heat dissipation is improved if the flexible part of the electric circuit board 4 is composed in large part of copper tracks, since the heat can also be dissipated along these copper tracks or copper lines of the electric circuit board 4. The flexible part of the circuit board 4 is thus essentially embodied for the electronics, wherein the circuit board 4 is also suitably thermally conductive due to the copper tracks, for which reason it is also excellently suited for temperature measurements.

Figure 8:
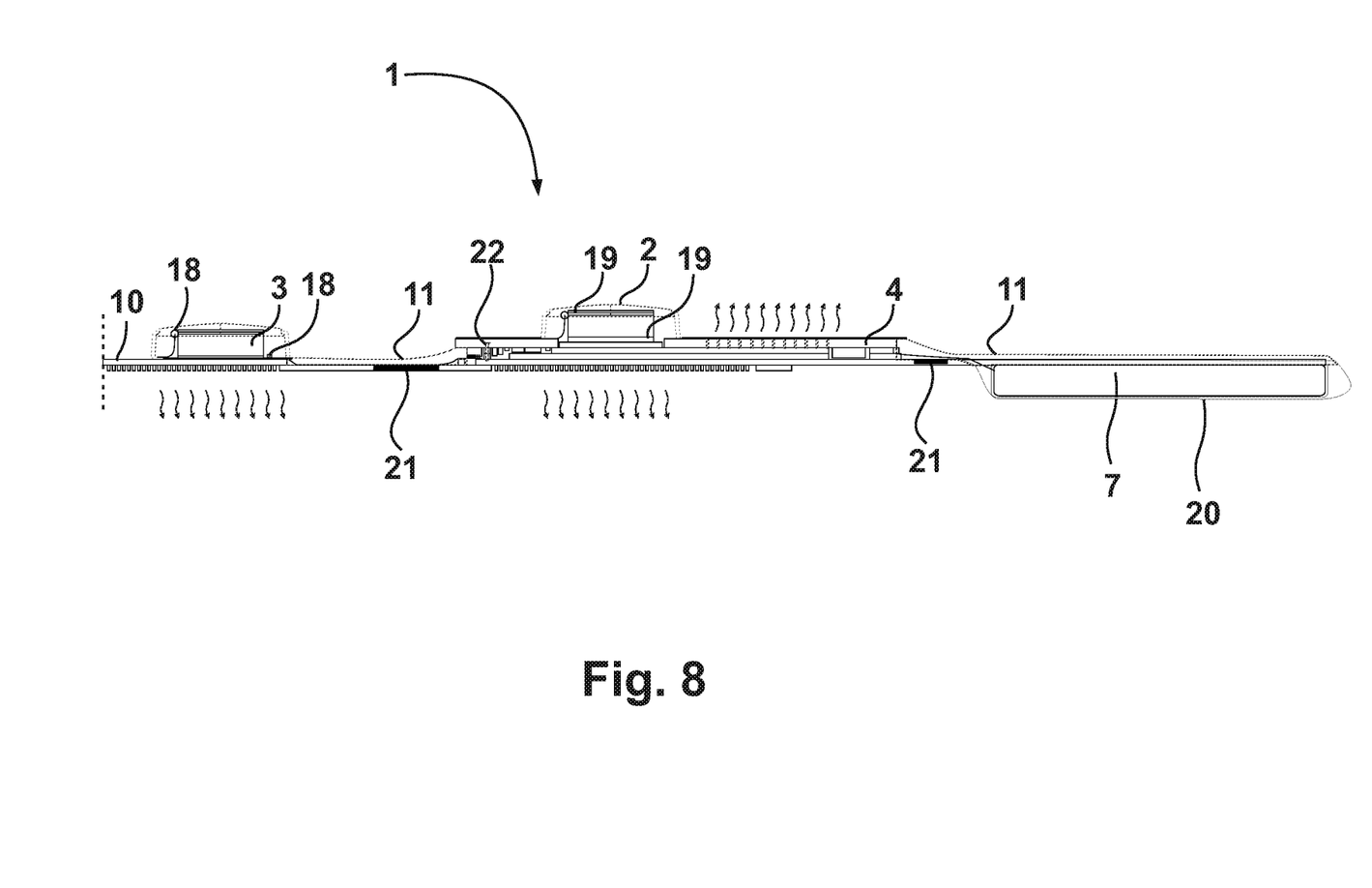
FIG. 8 shows a schematic illustration of a portion of another device according to the invention.

In FIG. 8, a first half of another embodiment of a device 1 is illustrated. The second half of the device 1 or the complete device 1 results from a mirroring of the first half on an axis which in FIG. 8 is illustrated by a dashed line, or by extending the device 1 across said line. The second half of the device 1 is essentially analogous to the first half of the device 1, but does not necessarily comprise all of the illustrated components. In this case, the mount 10 comprises a metal sheet structure, in particular made of an AlMgSi1 sheet. Individual parts of the mount 10, for example metal sheets, can thereby have different sizes and/or recesses, in order to maximize a surface that is in direct contact with an ambient air. The individual metal sheets of the mount 10 can preferably be glued, screwed, soldered, welded together or connected to one another in another manner. Alternatively, the mount 10 can be produced from one piece, for example, by milling and/or other machining methods. Active regions of a device 1 of this type can respectively comprise one Peltier element 3 and at least one temperature sensor 18. In addition, a skin contact material 2 can be provided which in particular is embodied as a preferably gold-plated skin contact plate. The skin contact plate can comprise a suitably thermally conductive material, in particular copper. Beneath the skin contact material 2, at least one thermal pad 19 can be arranged, for example. An insulating material 11 or a flexible plastic part, in particular made of a thermoplastic elastomer, can be arranged on a top side of the device 1, in particular in a flexible region, for example in the region of predetermined bow points 21. This flexible plastic part serves in particular as a soft support on a body part. The electric circuit board 4 is preferably embodied with thermal vias, as heat can thus be transferred through the circuit board 4 and emitted on the body side. A waste heat is in this case indicated by curved arrows. Here, one primary waste heat region is indicated on the body side and two primary waste heat regions are indicated on the ambient environment side. The circuit board 4 itself can preferably be formed from an anodized metal sheet. Preferably, this metal sheet has a thickness of 0.2 mm. In order to be fixed in place, the circuit board 4 can, for example, be connected to the mount 10 by at least one screw 22. In addition, an energy source 7, in particular a lithium polymer storage battery, is provided which is encased in a storage battery housing 20. The storage battery housing 20 can preferably be formed from a plastic, for example, from an acrylonitrile-butadiene-styrene copolymer (ABS), thermoplastic polyurethane (TPU) or the like, or can comprise one or more of these materials. In the device 1, it can be provided, for example, that only one energy source 7 is envisaged. Accordingly, the second half, which is not illustrated, can be embodied without an energy source. To provide a longer-lasting supply of energy, it can be provided that both halves comprise an energy source 7.

A device 1 according to the invention can, in addition to aforementioned applications, also be used for cooling, heating, and/or therapy for the following other body regions and/or ailments, for example:

insect bites;
in the hair region during a chemotherapy treatment, to protect against hair loss;
wound and scar cooling;
tension headache in the neck region;
jaw pain and toothaches;
ailments in the stomach region;
swelling in the event of a bone fracture;
in the testicular region for improving a sperm quality;
epididymitis;
testicular contusions;
ruptured testicle;
on joints;
sports injury;
muscle pain;
thrombosis;
multiple sclerosis;
fatigue.

The invention claimed is:

1. A device for cooling and/or heating a body region, said device comprising:
at least one thermally conductive skin contact material is made from a bendable metallic film that is configured to directly contact the skin, and at least one Peltier element;
the Peltier element being connected to the skin contact material;
a thermally conductive connecting element and a heat dissipation element are provided;
heat emitted via an outer side of the Peltier element is configured to be distributed to the heat dissipation element via the connecting element; and
the heat dissipation element is embodied to be bendable and is arranged on an outermost side of the device, together with at least one rigid cooling body.

2. The device according to claim 1, wherein:
the device is embodied to be free of liquid heat transfer media.

3. The device according to claim 1, wherein:
at least one circuit board is provided.

4. The device according to claim 1, wherein:
at least one cooling body is provided.

5. The device according to claim 1, wherein:
an energy source is provided for operating the Peltier element, wherein the energy source is connected to the Peltier element in particular via cables.

6. The device according to claim 1, wherein:
a control unit is provided.

7. The device according to claim 1, wherein:
at least one temperature sensor is provided.

8. The device according to claim 1, wherein:
a line is provided for a supply of pharmaceuticals.

9. The device according to claim 1, wherein:
an acoustic output device and/or a vibration output device are provided.

10. The device according to claim 1, wherein:
a mount is provided for securing the device to a body region.

11. The device according to claim 1, wherein:
the device is constructed in an at least partially layered manner.

12. The device according to claim 1, wherein:
the device for cooling and/or heating a body region is a device for cooling and/or heating a head region.

13. The device according to claim 1, wherein:
the thermally conductive connecting element is a thermally conductive film.

* * * * *